United States Patent
Li et al.

(10) Patent No.: US 6,630,063 B1
(45) Date of Patent: Oct. 7, 2003

(54) UNIFORM LASER EXCITATION AND DETECTION IN CAPILLARY ARRAY ELECTROPHORESIS SYSTEM AND METHOD

(75) Inventors: Qingbo Li, State College, PA (US); Songsan Zhou, Ferguson, PA (US); Changsheng Liu, State College, PA (US)

(73) Assignee: I. Reich Family Limited Partnership, New York, NY (US)

( * ) Notice: Subject to any disclaimer, the term of this patent is extended or adjusted under 35 U.S.C. 154(b) by 0 days.

(21) Appl. No.: 09/413,355

(22) Filed: Oct. 6, 1999

(51) Int. Cl.[7] .................. G01N 27/26; G01N 27/447
(52) U.S. Cl. .................. 204/452; 204/603; 356/344
(58) Field of Search ...................... 204/603, 452; 356/344

(56) References Cited

U.S. PATENT DOCUMENTS

| | | | |
|---|---|---|---|
| 5,242,567 A | 9/1993 | Fujimiya et al. | 204/612 |
| 5,538,613 A * | 7/1996 | Brumley et al. | 204/612 |
| 5,675,155 A | 10/1997 | Pentoney et al. | 250/458.1 |
| 5,900,934 A * | 5/1999 | Gilby et al. | 356/344 |
| 5,998,796 A * | 12/1999 | Liu et al. | 250/458.1 |
| 6,120,667 A * | 9/2000 | Hayashizaki et al. | 204/603 |

* cited by examiner

Primary Examiner—Nam Nguyen
Assistant Examiner—John S. Starsiak, Jr.
(74) Attorney, Agent, or Firm—Pennie & Edmonds LLP

(57) ABSTRACT

A capillary electrophoresis system comprises capillaries positioned in parallel to each other forming a plane. The capillaries are configured to allow samples to migrate. A light source is configured to illuminate the capillaries and the samples therein. This causes the samples to emit light. A lens is configured to receive the light emitted by the samples and positioned directly over a first group of the capillaries and obliquely over a second group of the capillaries. The light source is further configured to illuminate the second group of capillaries more than the first group of the capillaries such that amount of light received by the lens from the first group of capillaries is substantially identical to amount of light received from the second group of capillaries when an identical amount of the samples is migrating through the first and second group capillaries.

28 Claims, 10 Drawing Sheets

UNIFORM LASER EXCITATION AND DETECTION IN CAPILLARY ARRAY ELECTROPHORESIS SYSTEM AND METHOD

TECHNICAL FIELD

This invention relates to a laser illumination and detection system for performing sample analysis, such as DNA sequencing, DNA fingerprinting, absorption/emission spectroscopy, and the like. More particularly, it pertains to a laser illumination system that employs a laser scanner.

BACKGROUND

A conventional capillary array electrophoresis system is configured to perform a high-throughput analysis on biological samples, e.g., DNA sequencing, using a highly sensitive laser-induced fluorescence detection method. In particular, the samples to be analyzed either possess fluorescing functional groups (fluorophores) in their molecular structure or are tagged with fluorescent dyes. These samples are then excited with a laser beam which causes the samples to emit fluorescence light. The emitted fluorescence light is detected and subsequently analyzed.

The samples are illuminated by the laser beam either while they are still migrating through the capillaries, i.e., on-column detection, or after they elute from output ends of the capillaries, i.e., sheath-flow detection, as described by Dovichi et al. (U.S. Pat. No. 5,741,412).

For the on-column detection method, samples in the confocal microscope scanning method can be used as described in Mathies el al. (U.S. Pat. No. 5,274,240) In this method, samples in each capillary are sequentially excited and detected by a confocal scanning system. In another method, as described by Yeung et al,(U.S. Pat. No. 5,741,411) all the capillaries are illuminated by a laser beam and monitored by a 2-dimensional charged couple device (CCD) simultaneously.

FIG. 1 illustrates a conventional on-column detection system 1 that includes a laser light source 3 illuminating a capillary array 5 and samples therein and a camera lens 7 receiving the emitted light from the samples. Subsequently, the received light from the samples is captured by a CCD and analyzed.

FIG. 2 shows an intensity profile, amounts of light received across a viewing field of the camera 7. More specifically, the measurements are made by illuminating a laser beam on the array of capillaries 5 having the same quantity of samples migrating through each of the capillaries. The view field of the camera 7 is about 2 cm, i.e., the width of a 96 capillary array comprising capillaries with 200 $\mu$m outside diameters (o.d.)laid side by side. The position of 300 in FIG. 2 corresponds to the center of the array.

The resulting intensity profile shows that the amount of the light received from the location near the center of the array is more than that from capillaries at the periphery of the array.

At least two aspects of the conventional system 1 cause this effect. First, the laser beam has a Gaussian beam profile. In other words, a laser beam produced by a conventional laser illuminates the capillaries in the middle portion with about 1.5 times more intensity than the capillaries at the periphery of the array. Second, the amount of light captured by the camera varies based on the location of the capillaries. In particular, the amount of light received by the camera from a unit area of the capillaries at the periphery of the array is less than that from a unit area of the capillary at the center of the array, when an identical amount of light is emitted by the samples within the capillaries in each of the unit areas.

The above discussed shortcomings of the conventional system produce a non-uniform intensity profile. For instance, the amounts of light received from the center capillaries and periphery capillaries can differ by a factor of 2–4, as shown in FIG. 2.

The non-uniform intensity profile is not desirable, because in order to obtain sufficient amounts of light from the capillaries at the periphery of the array, the strength of the laser beam illuminating the center of the array may saturate the camera. Further, in order to process and analyze the data collected under this condition for capillary-to-capillary comparison and quantification, the subsequent analysis. process becomes complicated.

SUMMARY OF THE INVENTION

The present invention, therefore, provides a capillary electrophoresis system that includes capillaries positioned parallel to each other to form a plane. The capillaries are configured to allow samples to migrate therethrough. The system further includes a light source configured to illuminate the capillaries and the samples therein. This causes the samples to emit light. The system also includes a lens configured to receive the light emitted by the sample. The lens is positioned directly over a first group of the capillaries and obliquely over a second group of the capillaries. The light source is further configured to illuminate the second group of capillaries more than the first group of the capillaries such that amount of light received by the lens from the first group of capillaries is substantially identical to amount of light received from the second group of capillaries when an identical amount of the samples is migrating through the first and second group capillaries.

The light source further includes a laser configured to produce a laser beam and a scanning mirror optically coupled to the laser to receive the laser beam. The scanning mirror is configured to be oscillated and positioned to aim the received laser beam at the capillaries. The light source further includes a control device operatively coupled to the scanning mirror. The control device is configured to control the oscillation of the scanning mirror. This causes the laser beam from the scanning mirror to illuminate the plurality of capillaries.

The plane formed by the plurality of capillaries has a coincident axis extending parallel to the lengths of the capillaries. Further, the scanning mirror aims the laser beam through a scanning plane which is formed by a locus of the laser beam illuminating the capillaries. In turn, the laser beam impinges on the capillaries at an angle of 45°–90° formed between the scanning plane and the coincident axis. The plane formed by the plurality of capillaries also has a transverse axis extending parallel to the widths of the capillaries. Further, the scanning plane has a central beam line extending from the scanning mirror to a center point among the capillaries illuminated by the laser beam. The laser beam impinges on the capillaries at an angle of 1°–90° formed between the transverse axis and the central beam line.

The present invention also provides a capillary electrophoresis method that includes the steps of introducing samples to a plurality of capillaries positioned in parallel to each other forming a plane and forming a first group and a second group of capillaries, and causing the samples to migrate through the capillaries. The method also includes the step of illuminating the second group of capillaries more than the first group of the capillaries such that amount of light received by a lens from the first group of capillaries is substantially identical to amount of light received from the second group of capillaries when an identical amount of the samples is migrating through the first and second group capillaries. The lens is positioned directly above the first group of capillaries and obliquely over the second group of capillaries.

In one embodiment, the method also includes the steps of measuring amount of light received by the lens from the first and second groups of capillaries, while injecting an identical amount of the samples into the first and second capillaries, and while illuminating the first and second groups of capillaries with a substantially identical amount of light. Subsequently, a difference between the amount of light received by the lens from the first and second groups of capillaries is calculated.

Furthermore, the illuminating step further includes the steps of generating a compensating laser beam that substantially eliminates the calculated difference. The capillaries are illuminated by the compensating laser beam.

BRIEF DESCRIPTION OF THE DRAWINGS

The present invention can better be understood through the attached figures in which

FIG. 5A shows an exploded view of the scanning assembly;

FIGS. 9a–9c shows an intensity compensation procedure of the present invention.

DETAILED DESCRIPTION OF THE PREFERRED EMBODIMENT

Figure 3:
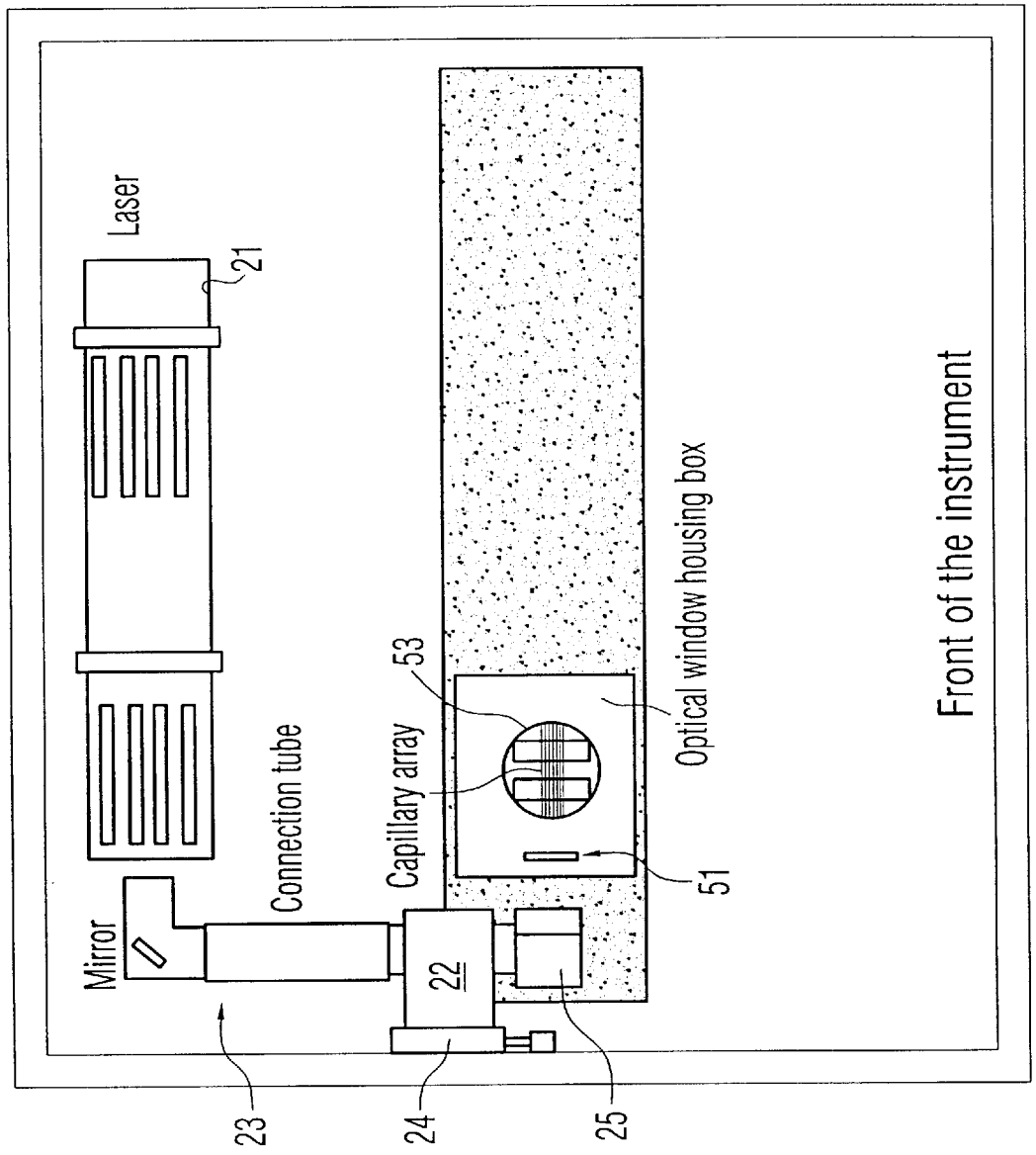
FIG. 3 shows a top view of the capillary electrophoresis system of the present invention.
Figure 4:
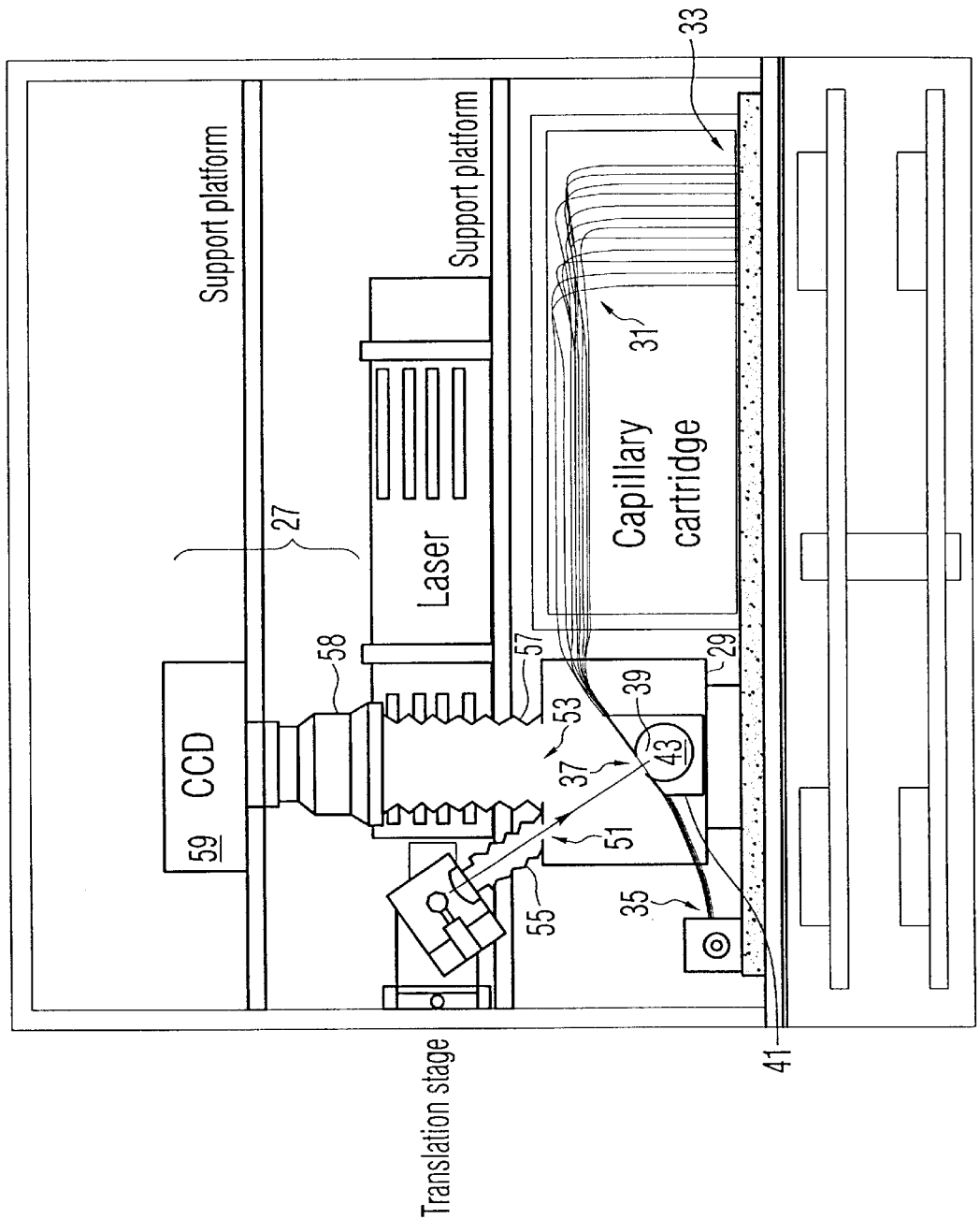
FIG. 4 shows a frontal view of the capillary electrophoresis system of the present invention.

Referring to FIGS. 3 and 4, the laser illumination and detection system of the present invention includes a laser 21, an optical coupler 23 and a scanner assembly 25. The system further includes a detection system 27 and a housing 29 which receives a number of capillaries 31. The capillaries 31 allows biological samples to migrate therethrough from input ends 33 to output ends 35. The samples are preferably biological samples, e.g., DNA samples, that either possess fluorescing functional groups (fluorophores) in their molecular structure or are tagged with fluorescent dyes.

The laser 21 preferably is an air-cooled argon ion laser that produces a light beam comprising of one, single emission mode, or multiple wavelengths, multi-wavelength emission mode. In the single wavelength emission mode, the wavelength is usually 488 nm or 514 nm. In the multi-wavelength emission mode, the wavelength may include any combination of 456 nm, 476 nm, 488 nm, 496 nm, 502 nm, 514 nm, with substantial power distributed at 488 nm and 514 nm wavelengths. Other lasers may also be used, depending upon the absorption wavelength of the samples to analyze. The optical beam produced by the laser 21 is delivered to the optical coupler 23.

Figure 5:
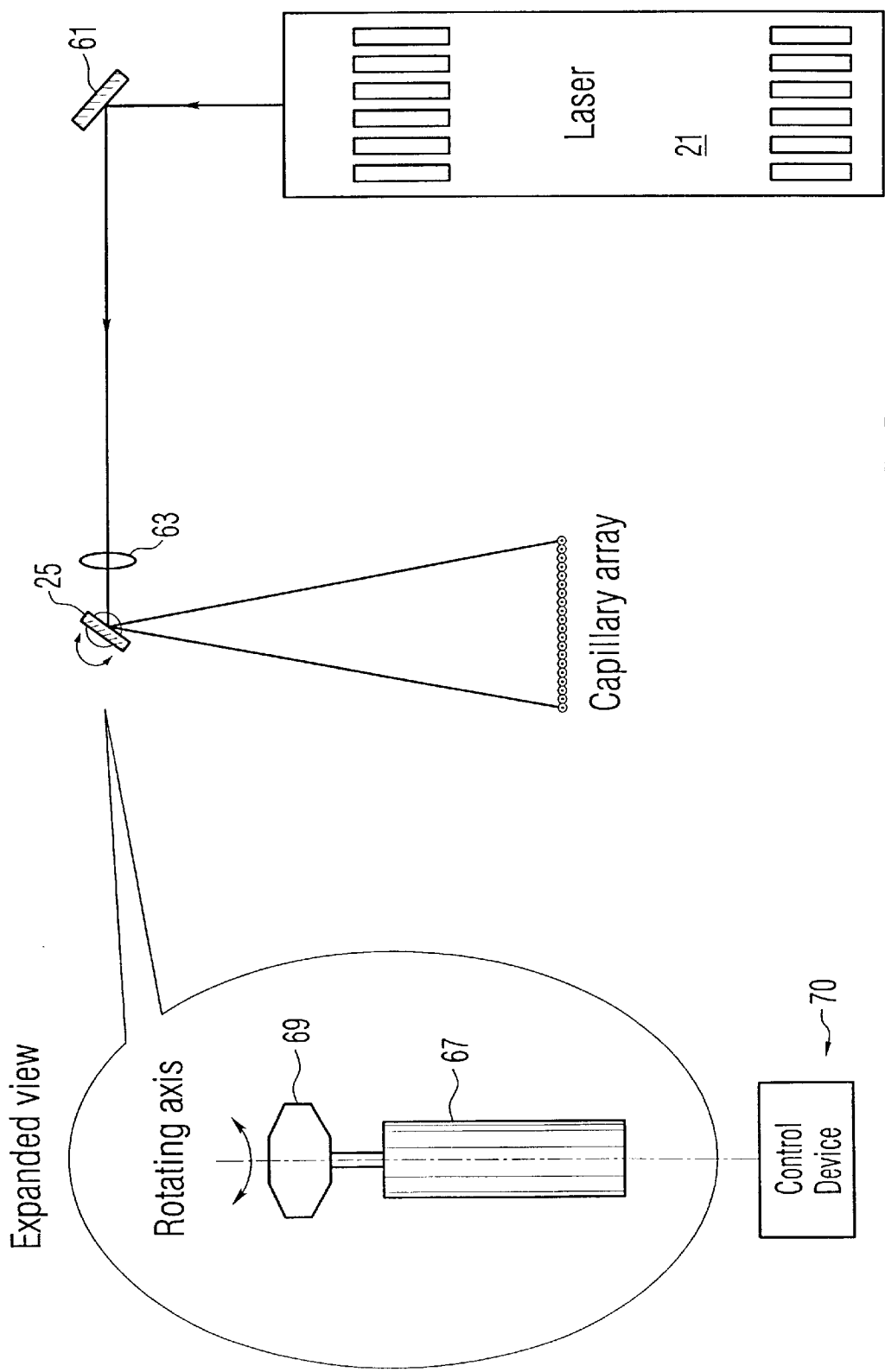
FIG. 5 shows an optical coupler that includes a scanner and a convex lens.

The optical coupler 23, in a preferred embodiment depicted in FIG. 5, includes a stationary mirror 61 and a convex lens 63. The mirror 61 reflects the laser beam produced by the laser 21 to the convex lens 63.

The scanner assembly 25 includes a scanning mirror 69 operatively mounted on a magnet rotor 67. The scanning mirror 69 is oscillated by the rotor 67. As the scanning mirror 69 oscillates, the laser beam received from the convex lens 63 is aimed at the capillaries and scans the capillaries. As a result, the scanning beam from the scanning mirror 69 illuminates the capillaries. In particular, the convex lens 63 is positioned at such a distance from the capillaries so as to allow the length of the light path, which is folded by the scanning mirror 69, from the convex lens 63 to the capillary array to be within the depth-of-focusing of the convex lens 63. Further, the scanning mirror 69 reflects the partially focused beam onto the capillaries. The laser beam then becomes focused optimally on capillaries where the laser beam impinges the capillaries.

The scanner assembly 25 is preferably a G120ST galvanometer scanner from General Scanning Inc. of Water Town, Mass. This scanner assembly is capable of rotating its scanning mirror up to 300 Hz. Its magnet rotor can be driven by a control device 70 that generates different waveforms described in the OEM Scanning Components & Subsystems catalog and in the MiniSAX servo controller manual, both of which are published by General Scanning. In alternative embodiments, scanner assemblies that can be driven to oscillate their respective scanning mirrors at scanning frequencies between 1–5000Hz are utilized.

The control device 70 can be a function generator such as Model-182A manufactured by WaveTek or a general purpose computer configured to generate various waveforms to be input to the rotor.

Figures 6, 6A:
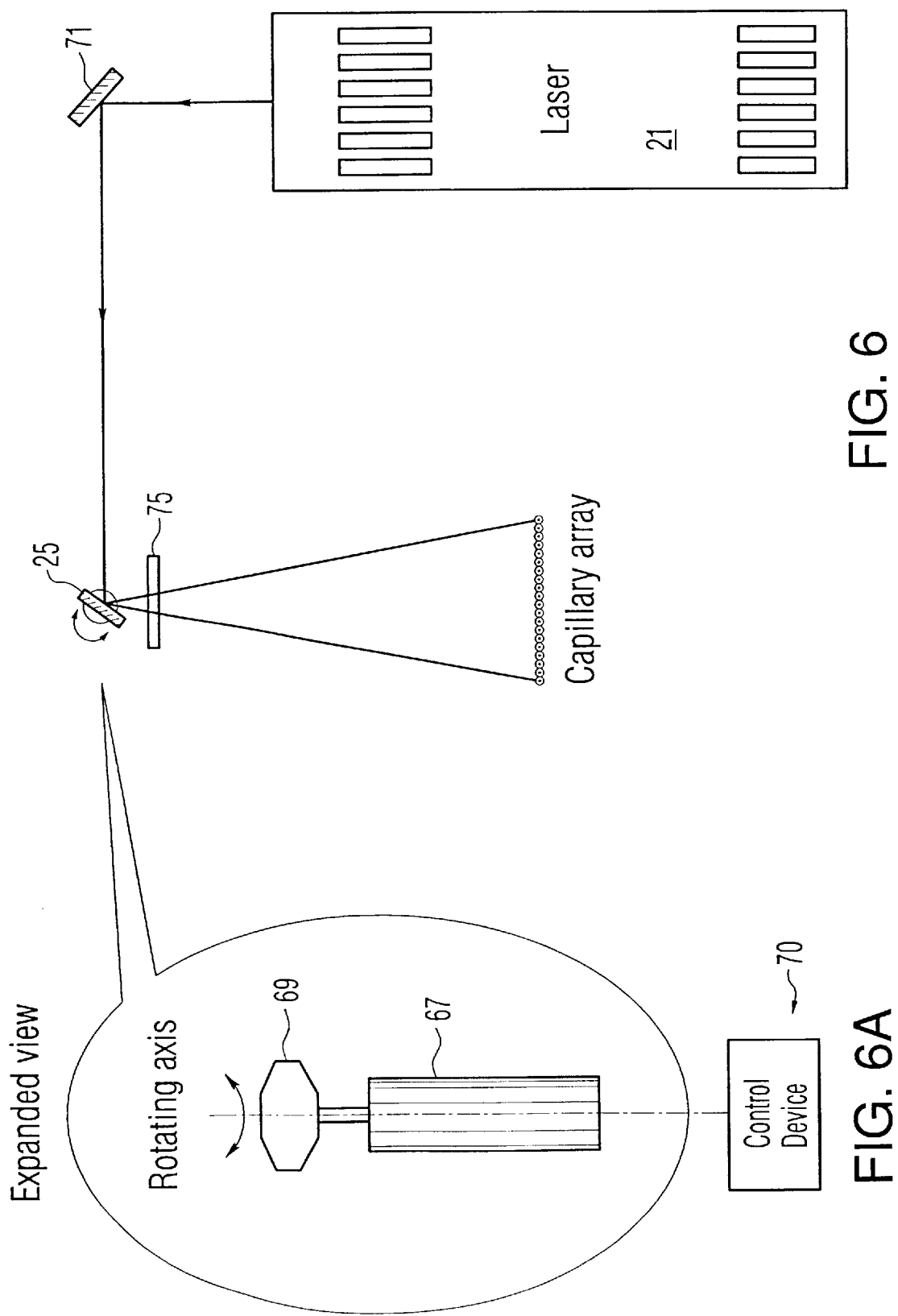
FIG. 6 shows an optical coupler that includes a scanner and a cylindrical lens.
FIG. 6A shows an exploded view of the scanning assembly.

In another preferred embodiment, as depicted in FIG. 6, the optical coupler 23 includes a stationary mirror 71 and a cylindrical lens 75. The laser beam produced from the laser 21 is reflected off of the stationary mirror 71. The reflected laser beam is then received by the scanner assembly 25. The laser beam is scanned by the scanning mirror 69 and then focused by the cylindrical lens 75. The focused laser beam illuminates the capillaries.

In an alternative embodiment, the optical coupler 23 may not include the convex lens 63 or the cylindrical lens 23. It should also be noted that, instead of the stationary mirror, an optical fiber, connected to the laser 21 at one end, can be used to deliver the laser beam to the scanner assembly 25. In another embodiment, an output end of the optical fiber can be configured to scan the capillaries by a mechanical device such that the laser beam from the optical fiber is delivered directly to the capillaries.

The capillaries 31 are fused-silica tubes with 100–500 um outside diameter (o.d.) and 5–250 um inside diameter (i.d.). In one embodiment, 96 capillaries with 150 um o.d., 50 um i.d. are provided. The capillaries 31 are received by the housing 29 and arranged parallel to each other in order to form a plane. In particular, the capillary centers are spaced apart from each other by 300 um. Hence, the total width of the capillary array arranged in parallel to form the plane is about 3 cm for the embodiment having 96 capillaries. It should be noted that an array of capillaries having 384 or more capillaries is also contemplated within this invention.

The external surfaces of the capillaries are coated with polyimide to provide mechanical strength and flexibility. When the capillaries are arranged to form a plane, a section of the polyimide coating is removed, e.g., 0.5–2.5 cm, from each capillary to create a translucent window for laser and fluorescent light to pass through. The translucent windows of the capillaries are aligned to form a line of windows 37.

Referring back to FIGS. 3 and 4, in the preferred embodiment, the optical coupler 23, in combination with the scanner assembly 25, aims and scans the laser beam to illuminate the width of the capillaries 31 forming the plane at the line of windows 37. The placement of the scanner assembly 25 is adjusted by a scanner assembly holder 22 and a translation stage 24, which ensure that the laser beam impinges the capillaries at the line of windows 37. The distance between the scanner assembly 25 and the line of windows 37 of the capillaries is 10–20 cm and, preferably, substantially equal to 15 cm.

Within the housing 29, a capillary mount 41 is provided to place the capillaries thereon. The capillary mount 41 has a sloped surface upon which the capillaries are placed. The slope is preferably 45°. The capillary mount 41 also includes a chamber 45 defined therein. In turn, the chamber 43 has an opening 39. The line of windows 37 of the capillaries are aligned with the opening 39 when the capillaries are placed on the capillary mount 41. As mentioned above, the light beam from the scanner assembly 25 is illuminated on the line of windows 37 of the capillaries. A portion of the laser beam is dissipated in illuminating the capillaries and samples therein. However, some portion of the laser beam passes through the capillaries. This portion of the laser beam enters the chamber 43. The chamber 43 is configured to capture the laser beam entered thereto. Note that without the chamber 43, the laser beam passing through the capillaries may be reflected toward the detection system 27, thereby interfering with detection and resulting in less than optimal performance.

The chamber 43 is preferably barrel shaped. In other words, the chamber 43 has a circular cross-section viewed from the front as shown in FIG. 4. The diameter of the circular cross-section is preferably 1–3 inches. In alternative embodiments, the chamber 43 can also have rectangular, triangular or other polygonal cross-section as long as a substantial portion of the laser beam which passes through the capillaries is prevented from reflecting toward the detection system 27. Moreover, the inside wall of the chamber can also be treated such that the laser beam impinging thereon would be absorbed rather than reflected.

The housing 29, having a substantially box shape, includes a pair of openings 51, 53 in the top side thereof. The openings 51, 53 are sized and shaped to receive light shielding tubes, i.e., light conduits 55, 57. More specifically, one end of the tube 55 is connected to the scanner assembly 25 and the other end of the tube 55 is connected to the opening 51 of the housing 29. The tube 55 is placed such that the laser beam from the scanner assembly 25 is allowed to illuminate the line of windows of the capillaries and shield outside light entering thereto. Further, one end of the tube 57 is connected to the detection system 27 and the other end of the tube 57 is connected to the opening 53 of the housing 29. The tube 57 is placed such that the light emitted by the samples is collected by the detection system 27 and outside light is prevented from entering thereto. Hence, the housing 29, in combination with the tubes 55, 57, provides a light shield. In other words, corruptive light from outside is prevented from entering the housing 29. The tubes 55, 57 are preferably bellows, i.e., an accordion like structure, such that they can be conveniently expanded and contracted to facilitate attaching and detaching to respective openings of the housing 29.

The detection system 27 includes a camera 58 that performs optical filtering and grating and a CCD 59. Preferably, the detection system 27 is a Pixel Vision CCD camera having a Nikon 85/1.4 lens assembly. Further, the distance between the lens assembly and the line of windows of the capillaries is 10–30 cm and, preferably, substantially equal to 20 cm.

Figure 7:
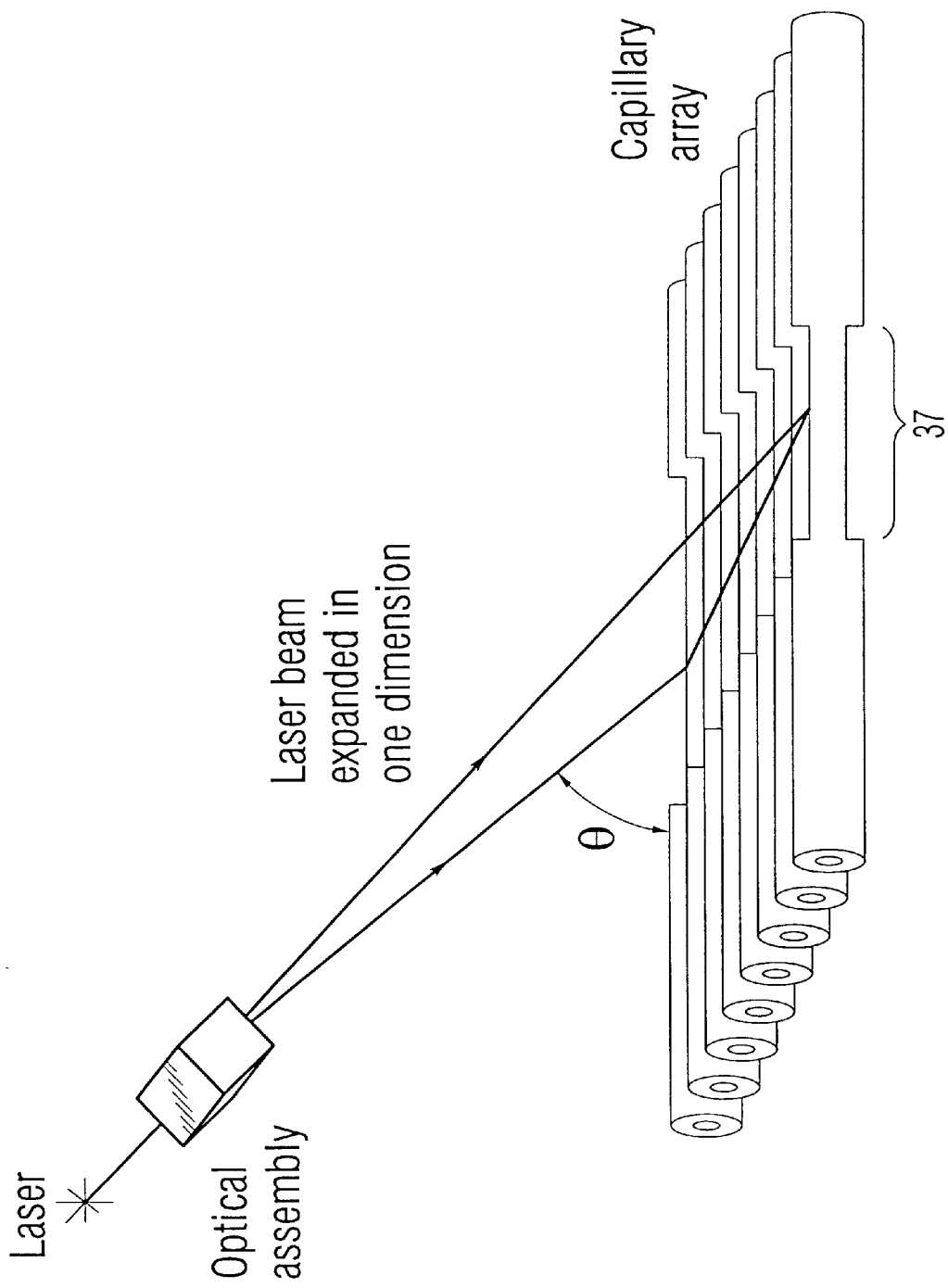
FIG. 7 illustrates an angle between the plane of the expanded laser beam and the capillary array.

Referring to FIG. 7, the laser beam from the scanner assembly 25 impinges on the line of windows 37 of the capillaries at an angle between 10° and 170°, preferably between 30° and 150° and more preferably between 45° and 135°. This angle is referenced as "θ" in FIG. 7.

Figure 8:
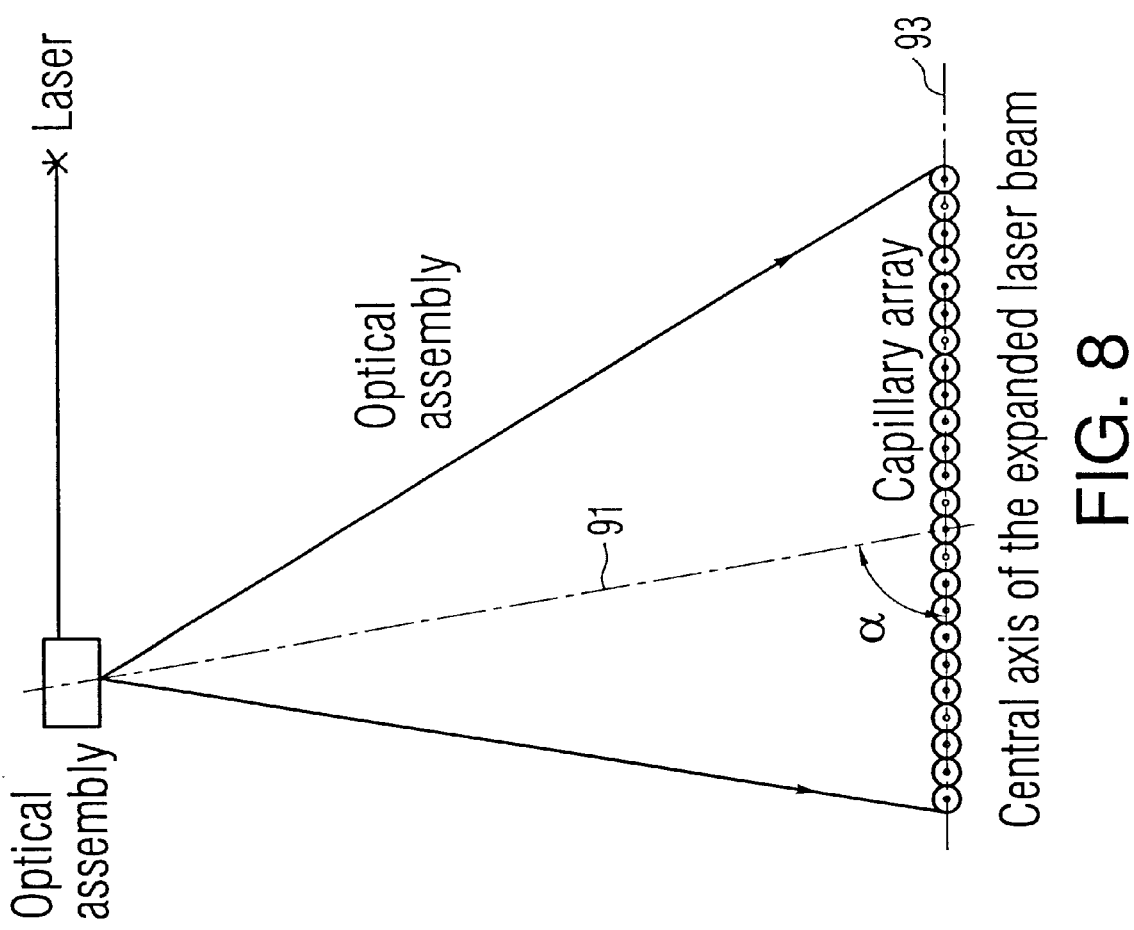
FIG. 8 illustrates an angle between the central beam of an expanded laser beam and the capillary array.

Now referring to FIG. 8, the center of the scanned laser beam is not required to be aligned with the center of the capillary array. In particular, a line 91, defined by connecting the center of the scanned laser beam and the center of the capillaries, can form an angle with respect to an axis 93 perpendicular to the length of the capillaries. This angle is designated as "α" in FIG. 8, and it can vary between 1° and 179°, and is preferably between 45° to 135°. Hence, the scanner assembly can be located anywhere to provide the laser beam that impinges the capillaries at the angles discussed above.

Figure 1:
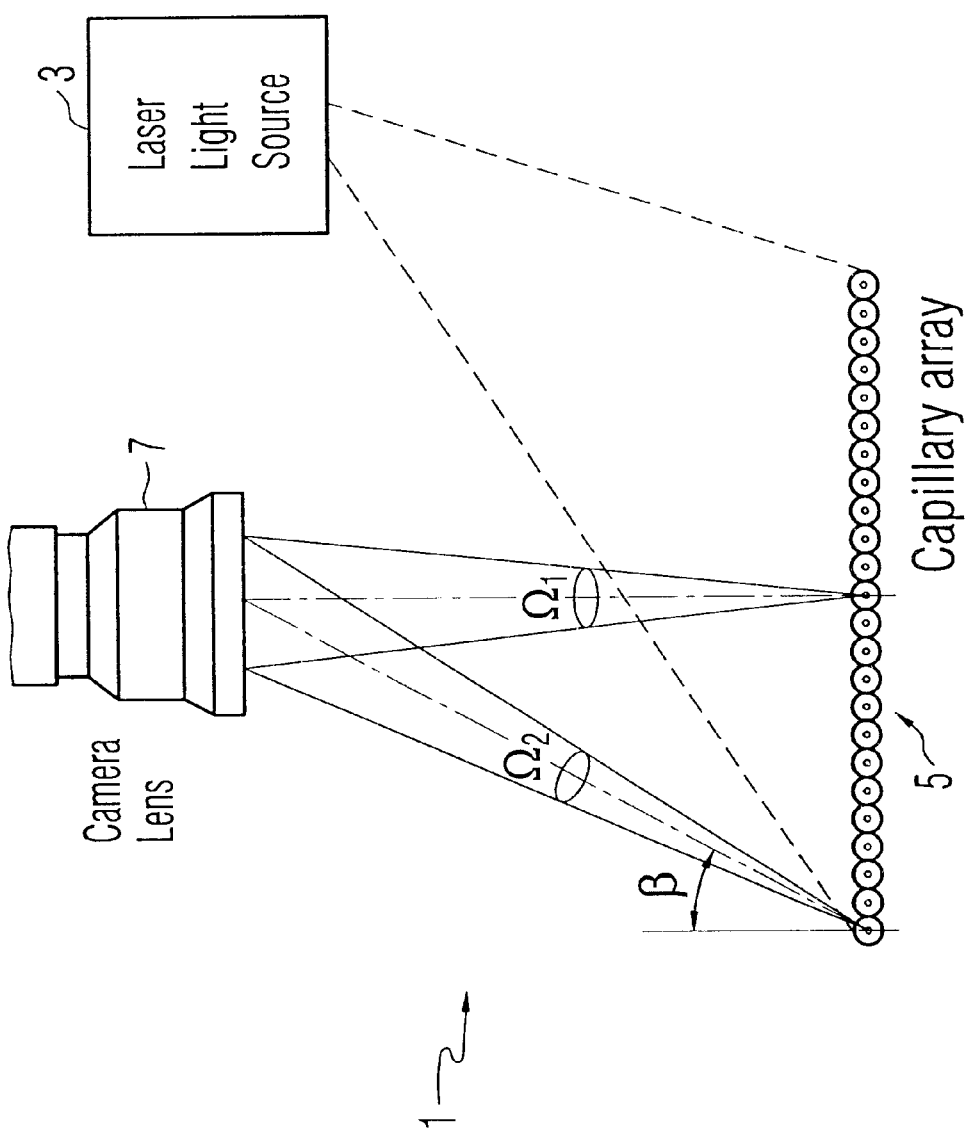
FIG. 1 shows a conventional capillary electrophoresis system.
Figure 2:
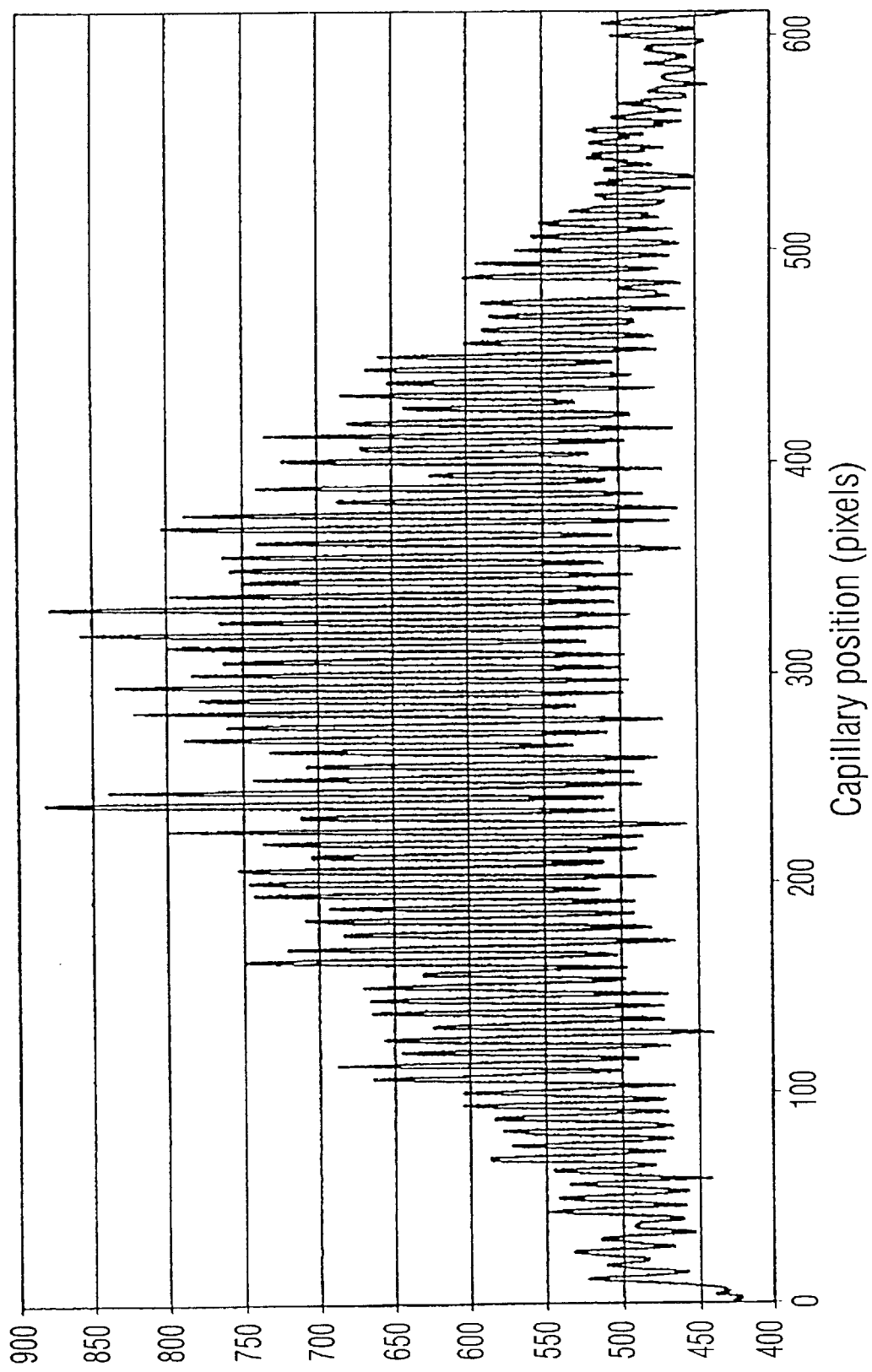
FIG. 2 illustrates a non-uniform intensity profile of a conventional system.

As discussed above in connection with FIGS. 1–2, there are two causes that produce the non-uniform intensity profiles. The first cause relates to the Gaussian beam profile of the conventional lasers. The second cause relates to the characteristics of lens optics wherein more light is received from the central capillaries than from the periphery capillaries. The non-uniformity profile effect becomes more pronounced as the number of capillaries increases, e.g., 384 or more.

Figure 9:
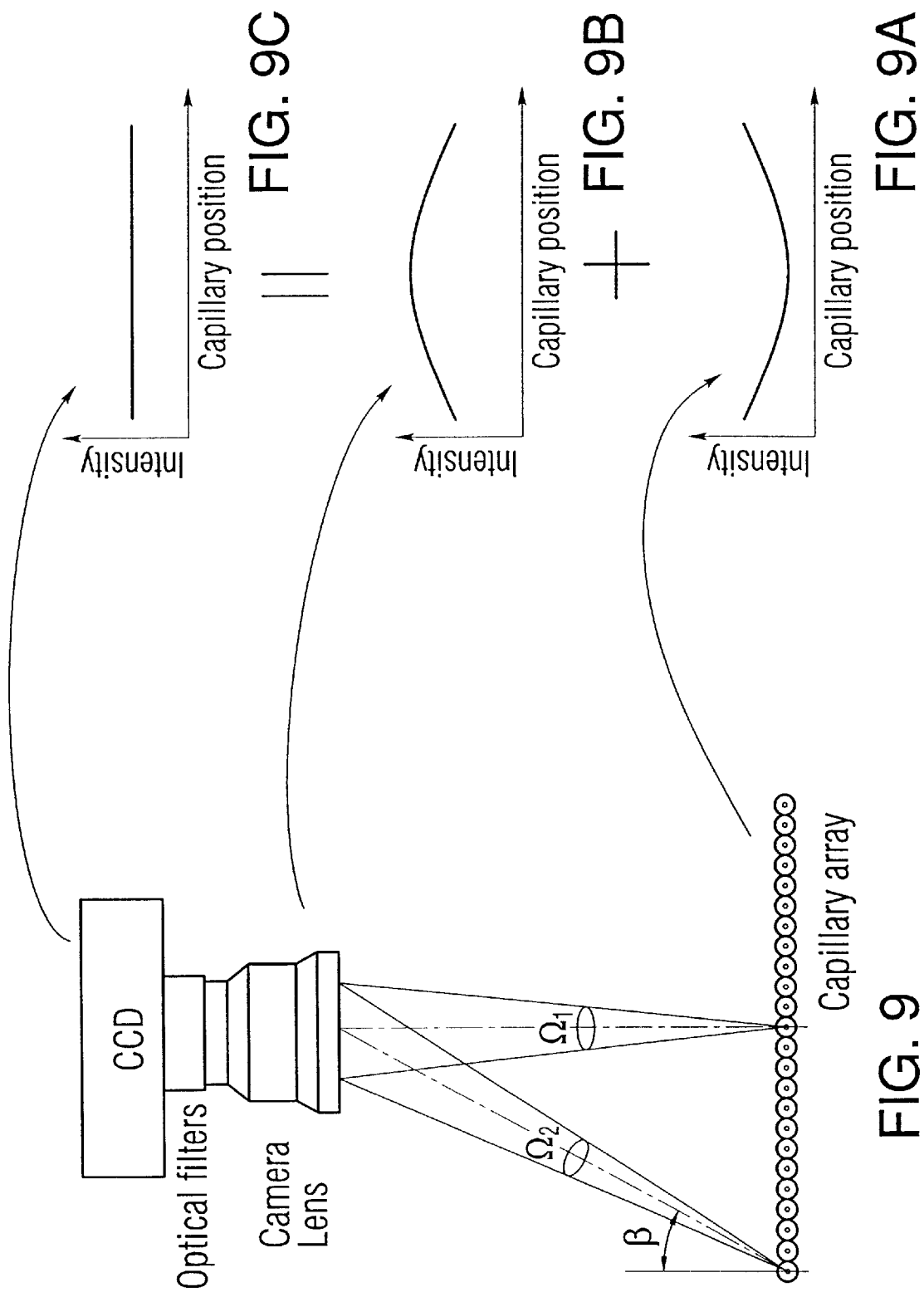
FIG. 9 illustrates generation of uniform intensity profile.

With respect to the Gaussian beam profile, the laser beam aimed and scanned by the scanner assembly 25 of the present invention does not have the Gaussian beam profile. Instead, the beam profile can be adjusted by the scanner assembly 25. In particular, referring to FIG. 9b, there is shown a typical intensity profile viewed from the camera using a laser beam from a conventional laser. This intensity profile is compensated by the laser beam aimed and scanned by the scanner assembly 25 illuminating the capillary array with a compensating intensity profile depicted in FIG. 9a. The net result is a uniform intensity profile as depicted in FIG. 9c.

In order to compensate for the non-uniform intensity profile, the system is calibrated. For this, the optical property of the camera lens assembly is first obtained. This can be done, for example, by running, a water solution containing $10^{-8}$ M fluorescein through the capillaries in order to determine the intensity profile of the lens assembly.

Based on the intensity profile obtain, the control device 70, i.e., the waveform generator, for the scanner assembly 25 is programmed to produce the compensating laser beam which will effectively neutralize the non-uniform intensity profile and produced a uniform intensity profile as a result. As seen in FIGS. 5 and 5A, the laser 21 creates a laser beam that is recieved by a scanneing mirror 69 which is oscillated in a controled manner by the control device 70 to create a compensating laser beam which illuminates that capillary array. It is noted that if a different lens assembly is utilized, then this procedure shall be repeated so as to properly calibrate the new lens assembly.

Subsequently, the oscillation of the scanning mirror 69 is controlled by the control device 70. For example, as the scanning mirror is oscillated in the direction to illuminate the periphery capillaries, the scanning mirror can be controlled to oscillate at a slow speed. Further, as the scanning mirror is oscillated in the direction to illuminated the center capillaries, the scanning mirror can be controlled to oscillate at a faster speed. In other words, the scanning mirror aims the laser beam at the capillaries located at the periphery of the array for longer time than the capillaries located at the center of the array. Therefore, the periphery capillaries are illuminated more than the central capillaries. In another embodiment, the intensity of the laser beam can be adjusted as well such that a higher intensity laser beam illuminates the periphery capillaries than the central capillaries. More specifically, as the scanning mirror aims the laser beam at the periphery capillaries, the output power of the laser is increased; and as the scanning mirror aims the laser beam as the central capillaries, the output power of the laser is decreased.

The scanner assembly, along with the control device 70, provides a flexible way to generate the compensating laser intensity profile. It should also be noted that even when the camera is not directly over the center of the capillary array, as discussed in connection with FIG. 8, the waveforms can be generated to produce an appropriate compensating intensity profile.

More specifically, the control device 70 produces a series of sinusoidal waveforms. The sinusoidal waveforms are then sent to the magnet rotor 67. The rotor then oscillates the scanning mirror 69 based on the sinusoidal waveforms. It should be noted that the control device 70 can produce different waveforms and the rotor can accept the different waveforms as well. Therefore, other waveforms including triangular waveforms, square waveforms can also be utilized to control the rotor. In particular, oscillating the scanning mirror 69 requires a non-zero differential voltage change. Therefore, a segment of square waveform can be used to localize the scanning mirror 69 at certain angle, thereby fixing a spot for the laser beam. Unlike the sinusoidal or triangular waveforms, a single amplitude square waveform is preferably not used to drive the rotor 67. But stacks of a series of square waveforms with changing amplitudes can drive the rotor. In general, any waveform can be divided into or made of a series of short square waveform segments that have changing amplitudes. Therefore, a digitized waveform generated from a computer can also drive the rotor.

An electrophoresis system having the above configuration can be tested by running a water solution that contains a predetermined amount of fluorescein samples through a capillary at the periphery of the array and through a capillary at the center of the array. If amount of light captured by the CCD from the two capillaries are substantially identical to each other, the calibration of the present invention is verified.

Figure 10:
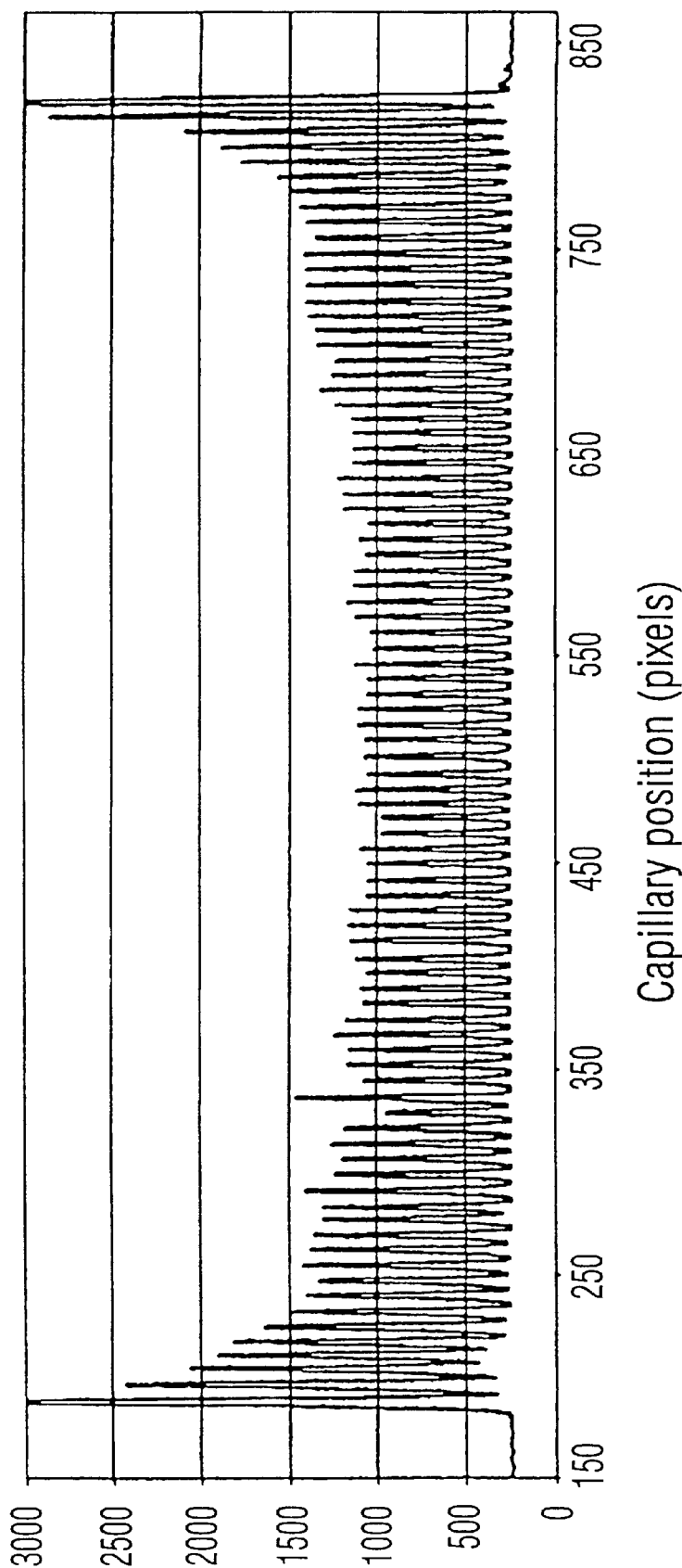
FIG. 10 illustrates an intensity profile using 150 Hz sinusoidal waveforms.

FIG. 10 shows the intensity profile that results from driving the rotor with a 150 Hz sinusoidal waveform. In other preferred embodiments, sinusoidal waveforms having 200 Hz or 250 Hz can be used. In another preferred embodiment, triangular waveforms at 150 Hz, 200 Hz or 250 Hz can be used. It should also be noted that a square wave or a combination of the sinusoidal, triangular and the square waveforms can also be used. For this, an SC2000 manufactured by General Scanning can be employed.

Note that other than several capillaries at the extreme periphery of the capillary array, FIG. 10 shows a uniform intensity profile. By further optimizing, i.e., increasing the scanning width, the spikes at the extreme periphery of the capillary array can also be eliminated. In particular, the scanning mirror can overshoot the capillary array so that the capillaries are illuminated with a uniform intensity profile.

In addition to providing improvements to large capillary array electrophoresis system, such as a 96-capillary or 384-capillary system, the present invention can also be applied to other electrophoresis platforms such as slab-gel and multi-channel electrophoresis on a glass chip.

While the above invention has been described with reference to certain preferred embodiments, it should be kept in mind that the scope of the present invention is not limited to these. For instance, the samples may be illuminated by the laser after emerging from the capillary tubes following migration, rather than while they are still within the capillary tubes. Thus, one skilled in the art may find variations of these preferred embodiments which, nevertheless, fall within the spirit of the present invention, whose scope is defined by the claims set forth below.

What is claimed is:

1. A capillary electrophoresis system, comprising:
   a plurality of capillaries positioned in parallel to each other forming a plane, wherein the capillaries are configured to allow samples to migrate therethrough;
   a light source configured to illuminate the capillaries and the samples therein, to thereby cause the samples to emit light; and
   a lens configured to receive the light emitted by the samples, wherein the lens is positioned directly over a first group of the capillaries and obliquely over a second group of the capillaries, wherein each of the first and second groups of capillaries comprises at least one of the capillaries, and
   wherein the light source is further configured to illuminate the second group of capillaries more than the first group of the capillaries such that amount of light received by the lens from the first group of capillaries is substantially identical to amount of light received from the second group of capillaries when an identical amount of the samples is migrating through the first and second groups of capillaries.

2. The system according to claim 1, wherein the light source further comprises:
   a laser configured to produce a laser beam;
   a scanning mirror optically coupled to the laser to receive the laser beam and configured to be oscillated, the scanning mirror positioned to aim the received laser beam at the capillaries; and
   a control device operatively coupled to the scanning mirror, the control device configured to control the oscillation of the scanning mirror, to thereby cause the laser beam from the scanning mirror to illuminate the plurality of capillaries.

3. The system according to claim 2, wherein the light source further comprises:

a stationary mirror optically coupling the laser to the scanning mirror; and a convex lens optically coupled to the stationary mirror and the scanning mirror.

4. The system according to claim 2, wherein the light source further comprises:

a cylindrical lens optically coupled to the scanning mirror, wherein the cylindrical lens is positioned to focus the laser beam on the plurality of capillaries.

5. The system according to claim 2, wherein the plane formed by the plurality of capillaries has a coincident axis extending parallel to the lengths of the capillaries, wherein the scanning mirror aims the laser beam through a scanning plane which is formed by a locus of the laser beam illuminating the capillaries, and wherein the laser beam impinges on the capillaries at an angle of 45°–90° formed between the scanning plane and the coincident axis.

6. The system according to claim 5, wherein the plane formed by the plurality of capillaries has a transverse axis extending parallel to the widths of the capillaries, wherein the scanning plane has a central beam line extending from the scanning mirror to a center point among the capillaries illuminated by the laser beam, and wherein the laser beam impinges on the capillaries at an angle of 1°–90° formed between the transverse axis and the central beam line.

7. The system according to claim 2, further comprising a magnet rotor connected to the scanning mirror, the rotor configured to oscillate the scanning mirror;

wherein the control device comprises:

a waveform generator coupled to the scanning mirror, the waveform generator configured to produce a sinusoidal waveform to drive the rotor.

8. The system according to claim 1 further comprising:

a mount having a surface configured to place the capillaries thereon and defining a chamber with an opening, wherein the chamber is configured to trap light when light enters through the opening.

9. The system according to claim 1 further comprising:

a housing configured to cover the capillaries illuminated by the light source, the housing defining a first opening and a second opening;

a first light conduit connected between the light source and the first opening;

a second light conduit connected between the lens and the second opening, wherein the housing and the first and second conduits provide a light shield.

10. The system according to claim 1, wherein the plurality of capillaries includes at least 384 capillaries.

11. A capillary electrophoresis method, comprising:

introducing samples to a plurality of capillaries positioned in parallel to each other forming a plane comprising a first group and a second group of capillaries, wherein the first and second groups each include at least one of the capillaries;

causing the samples to separate and migrate through the capillaries; and illuminating the separated samples within the first and second groups of capillaries with the separated samples in the second group of capillaries being illuminated more than the separated samples in the first group of capillaries such that an amount of light received by a lens from within the first group of capillaries is substantially identical to an amount of light received from within the second group of capillaries when an identical amount of the samples is migrating through the first and second group capillaries, wherein the lens is positioned directly above the first group of capillaries and obliquely over the second group of capillaries.

12. The method according to claim 11, further comprising the steps of:

prior to the step of illuminating the separated samples in the first and second groups of capillaries with the separated samples in the second group of capillaries being illuminated more than the separated samples in the first group of capillaries:

measuring an amount of light received by the lens from within the first and second groups of capillaries in response to:

injecting an identical amount of the samples into the first and second capillaries; and illuminating the separated samples in the first and second groups of capillaries with substantially identical amounts of light;and subsequently calculating a difference between a first amount of light received by the lens from within the first group of capillaries and a second amount of light received by the lens from within the second group of capillaries.

13. The method according to claim 12, wherein the step of illuminating the separated samples in the first and second groups of capillaries with the separated samples in the second group of capillaries being illuminated more than the separated samples in the first group of capillaries comprises:

generating a compensating laser beam that substantially eliminates the calculated difference between the amount of light received by the lens from within the first and second groups of capillaries, wherein only the compensating laser beam is used to illuminate the separated samples within the first and second groups of capillaries with the separated samples within the second group of capillaries being illuminated more than the separated samples within the first group of capillaries.

14. The method according to claim 13, wherein the step of generating the compensating laser beam further comprises:

producing a laser beam;

receiving the laser beam by a scanning mirror; and oscillating the scanning mirror to generate the compensating laser beam.

15. The method according to claim 14, wherein the step of oscillating the scanning mirror further comprises:

generating a controlling waveform to control the oscillation of the scanning mirror, wherein the controlling waveform is one of sinusoidal and triangular waveforms.

16. The method according to claim 14, wherein the step of oscillating the scanning mirror further comprises:

generating a controlling waveform to control the oscillation of the scanning mirror, wherein the controlling waveform is a combination of sinusoidal, square and triangular waveforms.

17. A capillary electrophoresis method comprising:

providing a plurality of capillaries arranged parallel to one another, the plurality of capillaries including a first group of capillaries and a second group of capillaries;

providing a lens positioned directly above the first group of capillaries and obliquely over the second group of capillaries;

introducing samples into said first and second groups of capillaries;

causing the samples to separate and migrate through the first and second groups of capillaries; and illuminating the separated samples in the first and second groups of capillaries with the separated samples in the second group of capillaries being illuminated for a longer time than the separated samples in the first group of capillaries such that:

a first amount of light received by the lens from within the first group of capillaries is substantially the same as a second amount of light received by the lens from within the second group of capillaries, when substantially identical sample amounts are introduced into the first and second groups of capillaries.

18. The method according to claim 17, wherein the illuminating step comprises:

producing a laser beam;

receiving first laser beam by a scanning mirror; and oscillating the scanning mirror to direct said laser beam towards said plurality of capillaries.

19. The method according to claim 18, wherein the step of oscillating the scanning mirror further comprises generating a controlling waveform to control the oscillation of the scanning mirror, wherein the controlling waveform is one of sinusoidal and triangular waveforms.

20. The method according to claim 18, wherein the step of oscillating the scanning mirror further comprises generating a controlling waveform to control the oscillation of the scanning mirror, wherein the controlling waveform is a combination of sinusoidal, square and triangular waveforms.

21. A method of controlling oscillation of a scanning mirror configured to direct a laser beam toward a planar arrangement of parallely aligned capillaries including a first group of capillaries and a second group of capillaries, the method comprising:

injecting identical amounts of a sample into the first and second groups of capillaries;

causing said sample to migrate through the first and second groups of capillaries;

illuminating, with substantially identical amounts of light, the samples after they have migrated through the first and second groups of capillaries;

measuring, at a point positioned directly above the first group of capillaries and obliquely over the second group of capillaries, a first amount of light received from the first group of capillaries, and a second amount of light received from the second group of capillaries;

calculating a difference between the first and second amounts of light;

creating a controlling waveform, based on said difference, to control oscillation of the scanning mirror such that said laser beam illuminates the second group of capillaries for a longer time than said laser beam illuminates the first group of capillaries, to thereby compensate for said difference.

22. A capillary electrophoresis system, comprising:

a plurality of capillaries arranged parallel to one another to thereby form a plane, the plurality of capillaries including a first capillary extending along a first portion of the plane, and a second capillary extending along a second portion of the plane;

a light source configured to illuminate a section of each of said first and second capillaries, with the second capillary being illuminated for a longer time than the first capillary such that:

a first amount of light received from within the first capillary is substantially similar to a second amount of light received from within the second capillary, when identical quantities of a sample migrate through said sections of the first and second capillaries and are illuminated by the light source, wherein the first and second amounts of light are measured at a point positioned directly over the first capillary and obliquely over the second capillary.

23. The system according to claim 22, wherein the light source comprises:

a laser configured to produce a laser beam;

a scanning mirror optically coupled to the laser to receive the laser beam and configured to be oscillated, the scanning mirror positioned to aim the received laser beam at the capillaries; and a control device operatively coupled to the scanning mirror, the control device configured to control the oscillation of the scanning mirror, to thereby cause the laser beam from the scanning mirror to illuminate the plurality of capillaries.

24. The system according to claim 23, wherein the light source further comprises:

a stationary mirror optically coupling the laser to the scanning mirror; and a convex lens optically coupled to the stationary mirror and the scanning mirror.

25. The system according to claim 23, wherein the light source further comprises:

a cylindrical lens optically coupled to the scanning mirror, wherein the cylindrical lens is positioned to focus the laser beam on the plurality of capillaries.

26. The system according to claim 23, wherein the plane formed by the plurality of capillaries has a coincident axis extending parallel to lengths of the capillaries, wherein the scanning mirror aims the laser beam through a scanning plane which is formed by a locus of the laser beam illuminating the capillaries, and wherein the laser beam impinges on the capillaries at an angle of 45°–90° formed between the scanning plane and the coincident axis.

27. The system according to claim 26, wherein the plane formed by the plurality of capillaries has a transverse axis extending parallel to widths of the capillaries, wherein the scanning plane has a central beam line extending from the scanning mirror to a center point among the capillaries illuminated by the laser beam, and wherein the laser beam impinges on the capillaries at an angle of 1°–90° formed between the transverse axis and the central beam line.

28. The system according to claim 23, further comprising a magnet rotor connected to the scanning mirror, the rotor configured to oscillate the scanning mirror, and wherein the control device comprises a waveform generator coupled to the scanning mirror, the waveform generator configured to produce a sinusoidal waveform to drive the rotor.

* * * * *